US009675585B1

(12) United States Patent
Fix et al.

(10) Patent No.: US 9,675,585 B1
(45) Date of Patent: Jun. 13, 2017

(54) EXTENDED RELEASE PHARMACEUTICAL FORMULATIONS

(71) Applicants: Ezra Pharma, Little Rock, AR (US); Rubicon Research Private Limited, Mumbai (IN)

(72) Inventors: Joseph A. Fix, Lawrence, KS (US); Shirish A. Shah, Phoenix, AZ (US); Pratibha S. Pilgaonkar, Mumbai (IN); Anilkumar S. Gandhi, Mumbai (IN)

(73) Assignees: Ezra Pharma, Little Rock, AR (US); Rubicon Research Private Limited, Mumbai (IN)

( * ) Notice: Subject to any disclaimer, the term of this patent is extended or adjusted under 35 U.S.C. 154(b) by 0 days.

(21) Appl. No.: 15/080,158

(22) Filed: Mar. 24, 2016

(51) Int. Cl.
A61K 9/20 (2006.01)
A61P 9/12 (2006.01)
A61K 31/41 (2006.01)
A61K 9/00 (2006.01)
A61K 9/28 (2006.01)

(52) U.S. Cl.
CPC ............ *A61K 31/41* (2013.01); *A61K 9/0065* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 9/2866* (2013.01); *A61K 9/2886* (2013.01)

(58) Field of Classification Search
None
See application file for complete search history.

(56) References Cited

U.S. PATENT DOCUMENTS

| 4,803,081 | A | 2/1989 | Falk et al. |
| 4,973,469 | A | 11/1990 | Mulligan et al. |
| 5,736,161 | A | 4/1998 | Garces et al. |
| 5,780,057 | A | 7/1998 | Conte et al. |
| 5,945,125 | A | 8/1999 | Kim |
| 5,972,389 | A | 10/1999 | Shell et al. |
| 6,022,562 | A | 2/2000 | Autant et al. |
| 6,107,276 | A | 8/2000 | Carli et al. |
| 6,120,803 | A | 9/2000 | Wong et al. |
| 6,340,475 | B2 | 1/2002 | Shell et al. |
| 6,383,471 | B1 | 5/2002 | Chen et al. |
| 6,465,502 | B1 | 10/2002 | Bullock et al. |
| 6,630,475 | B2 | 10/2003 | Neustadt et al. |
| 6,635,280 | B2 | 10/2003 | Shell et al. |
| 6,692,767 | B2 | 2/2004 | Burnside et al. |
| 6,699,503 | B1 | 3/2004 | Sako et al. |
| 6,723,340 | B2 | 4/2004 | Gusler et al. |
| 6,881,420 | B2 | 4/2005 | Flashner-Barak et al. |
| 7,157,100 | B2 | 1/2007 | Doshi et al. |
| 7,728,021 | B2 | 6/2010 | Dalmases Barjoan et al. |
| 2001/0018070 | A1 | 8/2001 | Shell et al. |
| 2003/0152622 | A1 | 8/2003 | Louie-Helm et al. |
| 2003/0158244 | A1 | 8/2003 | Devane et al. |
| 2003/0180352 | A1 | 9/2003 | Patel et al. |
| 2003/0232081 | A1 | 12/2003 | Doshi et al. |
| 2004/0001888 | A1 | 1/2004 | Jin |
| 2005/0013863 | A1 | 1/2005 | Lim et al. |
| 2005/0096365 | A1 | 5/2005 | Fikstad et al. |
| 2006/0281801 | A1 | 12/2006 | Kumar et al. |
| 2007/0166372 | A1 | 7/2007 | Huang et al. |
| 2010/0233253 | A1 | 9/2010 | Kavimandan et al. |
| 2010/0291225 | A1* | 11/2010 | Fanda ............... A61K 9/2027 424/498 |
| 2011/0027358 | A1 | 2/2011 | Kshirsagar et al. |
| 2011/0171275 | A1* | 7/2011 | Jiang ............... A61K 9/0065 424/400 |
| 2012/0195968 | A1* | 8/2012 | Shah ............... A61K 9/2013 424/484 |
| 2013/0136795 | A1 | 5/2013 | Barrero et al. |
| 2014/0371282 | A1 | 12/2014 | Pilgaonkar et al. |

FOREIGN PATENT DOCUMENTS

| WO | 9907342 A1 | 2/1999 |
| WO | 0122791 A2 | 4/2001 |
| WO | 03000294 A1 | 1/2003 |
| WO | 03039521 A1 | 5/2003 |
| WO | 2006113631 A2 | 10/2006 |
| WO | 2007077581 A2 | 7/2007 |
| WO | 2008064338 A2 | 5/2008 |
| WO | 2008084504 A2 | 7/2008 |
| WO | 2009084040 A1 | 7/2009 |
| WO | WO2009084040 * | 7/2009 |
| WO | 2009135646 A2 | 11/2009 |

OTHER PUBLICATIONS

Colorcon, Opadry II, 2009.*
L. H.V. Reddy and R.S.R. Murthy, "Floating Dosage Systems in Drug Discovery," Critical Reviews in Therapeutic Drug Carrier Systems (2002) 19(6): 553-585. Abstract Only.
The National Formulary 24, United States Pharmacopeia 29 <711> 2673 (United States Pharmacopeial Convention 2006).
Don C. Cox & William B. Furman, Systematic Error Associated with Apparatus 2 of the USP Dissolution Test I: Effects of Physical Alignment of the Dissolution Apparatus, 71 J. Pharm. Scis. 451 (1982).
Don C. Cox et al., Systematic Error Associated with Apparatus 2 of the USP Dissolution Test III: Limitations of Calibrators and the USP Suitability Test, 72 J. Pharm. Scis. 910 (1983).

(Continued)

*Primary Examiner* — Jianfeng Song
(74) *Attorney, Agent, or Firm* — Amin Talati Upadhye LLP; Adam D. Sussman; George M. Carrera, Jr.

(57) ABSTRACT

The present invention relates to coated extended release pharmaceutical formulations of valsartan comprising a core comprising valsartan and at least one coating layer over the core. The present invention further relates to extended release pharmaceutical formulations comprising (a) a core comprising valsartan and at least one hydrophilic swelling polymer and (b) at least one coating layer over the core wherein the coating layer in contact with the core is applied from an organic solvent based system.

25 Claims, No Drawings

(56) References Cited

OTHER PUBLICATIONS

Saeed A. Qureshi & Iain J. McGilveray, Typical variability in drug dissolution testing: study with USP and FDA calibrator tablets and a marketed drug (glibenclamide) product, 7 Eur. J. Pharm. Scis. 249 (1999).

Saeed A. Qureshi & Javad Shabnam, Cause of high variability in drug dissolution testing and its impact on setting tolerances, 12 Eur. J. Pharm. Scis. 271 (2001).

Paulo Costa & J.M. Sousa Lobo, Influence of Dissolution Medium Agitation on Release Profiles of Sustained-Release Tablets, 27 Drug Development & Industrial Pharmacy 811 (2001).

J. Kukura et al., Shear distribution and variability in the USP Apparatus 2 under turbulent conditions, 279 Int'l J. Pharmaceutics 9 (2004).

Jennifer L. Baxter et al., Hydrodynamics-induced variability in the USP apparatus II dissolution test, 292 Int'l J. Pharmaceutics 17 (2005).

Ge Bai et al., Hydrodynamic Investigation of USP Dissolution Test Apparatus II, 96 J. Pharm. Scis. 2327 (2007).

Ge Bai & Piero M. Armenante, Hydrodynamic, Mass Transfer, and Dissolution Effects Induced by Tablet Location during Dissolution Testing, 98 J. Pharm. Scis. 1511 (2009).

Piero Armenante & Fernando Muzzio, Inherent Variability in Dissolutino Testing: The Effect of Hydrodynamics in the USP II Apparatus (2005), available at http://www.fda.gov/ohrms/dockets/ac/05/briefing/2005-4187B1_01_04-Effect-Hydrodynamics.pdf.

* cited by examiner

EXTENDED RELEASE PHARMACEUTICAL FORMULATIONS

FIELD OF THE INVENTION

The present invention relates to coated extended release pharmaceutical formulations of valsartan. The invention further relates to extended release pharmaceutical formulations comprising a core comprising valsartan and at least one coating layer over the core. Particularly the present invention relates to extended release pharmaceutical formulations comprising (a) a core comprising valsartan and at least one hydrophilic swelling polymer and (b) at least one coating layer over the core wherein the coating layer in contact with the core is applied from an organic solvent based system. The present invention also relates to extended release pharmaceutical formulations comprising a core comprising valsartan and at least one hydrophilic swelling polymer and dual layer coating over the core.

BACKGROUND OF THE INVENTION

Angiotensin II is a very potent peptide hormone that causes the muscles surrounding the blood vessels to contract, which thereby significantly narrow the blood vessels. This narrowing increases the pressure within arterial vessels, causing high blood pressure (hypertension). Angiotensin receptor blockers (ARBs) are drugs that block the action of angiotensin II. As a result, arterial vessels dilate and blood pressure is reduced, thereby making it easier for the heart to pump blood. ARBs are therefore used to prevent heart failure as well as hypertension. Drugs in this class include candesartan (Atacand, Astra-Zeneca), eprosartan (Teveten, Solvay & Biovail), irbesartan (Avapro, BMS), losartan (Cozaar, Merck), olmesartan (Benicar, Medoxomil; Sankyo & Forest), telmisartan (Micardis, Boehringer Ingelheim), valsartan (Diovan, Novartis) and pratosartan (Kotobuki). ARBs are used alone or in combination with other classes of antihypertensive agents that include thiazide diuretics, β blockers, calcium channel blockers, rennin inhibitor, and ACE inhibitors, both for the treatment of hypertension and congestive heart failure.

Valsartan, a selective ARB, is a well-known antihypertensive agent. Valsartan is rapidly absorbed from the gastrointestinal tract after oral administration. The absolute bioavailability of valsartan is about 25% (10-35%). This relatively low bioavailability of valsartan is primarily due to its poor solubility in the acid milieu of the stomach. Valsartan is an acid, and therefore, has good solubility at pH>5 and low solubility in acidic conditions of the stomach. Valsartan becomes ionized in small intestine and hence cannot get absorbed in ionized form. Valsartan typically gets absorbed rapidly with Tmax in the range of 2-4 hours, however following Cmax the plasma concentration starts reducing reaching to very low level after 10-12 hours.

Pharmaceutically active agents which exhibit low bioavailability unfortunately create a need for frequent dosing of a large amount of pharmaceuticals in order to provide and maintain therapeutic levels. The need for frequent dosing presents patient compliance problems. A need for extended release formulations of valsartan thus arises. Valsartan has low solubility associated with window of absorption, both resulting in poor bioavailability and variability in drug response. Therefore, it becomes important to not only increase the solubility of valsartan but also to take advantage of the window of absorption to increase bioavailability, extend drug release and design true once a day compositions.

Some attempts have been made to provide extended release compositions of valsartan. Design of such extended release formulations of valsartan requires the use of number of different polymers or excipients of varied nature and type. US patent publication 20100233253 discusses a gastroretentive drug delivery system for delivering valsartan or a pharmaceutically acceptable salt thereof to the stomach, duodenum and upper small intestine of a patient comprising a release portion comprising valsartan and a swellable gastro-retentive portion wherein the swelling of the gastroretentive portion results in an increase of total volume of the system of less that 50%. PCT Publication WO02009084040A1 discusses a gastro-retentive oral dosage form, comprising an active layer and a gastroretentive layer. The active layer comprises valsartan, solubilizer and at least one release retardant and the gastroretentive layer comprises at least one swelling polymer, at least one swelling enhancer and at least one gas generating agent and optionally an acid source. The gastroretentive dosage form swells in the presence of gastric fluid such that the size of the dosage form is sufficiently increased to provide retention of the dosage form in the upper gastrointestinal tract for a time period of about 30 minutes to about 12 hours. Developing such extended release formulations of the gastroretentive type requiring incorporation of large amounts of swelling type of polymers results in dosage forms that are larger in size than any conventional dosage forms. Such large sized tablets may generally create problems associated with swallowing of the tablets. Coating such tablets to improve swallowability, patient acceptability and compliance therefore becomes imperative. However, coating tablets of extended release type comprising increased amounts of hydrophilic swellable polymers presents numerous challenges.

Various coated solid dosage forms of valsartan have been discussed. US Patent Publication 20130136795 discloses an immediate release solid pharmaceutical composition comprising a core containing valsartan or a pharmaceutically acceptable salt thereof prepared by wet granulation, characterized in that the core has a moisture content of 3% or less and coated with film coating composition which may comprise up to 3% moisture or may be moisture impermeable. US Patent Publication 2011027358 discusses immediate release pharmaceutical tablet composition comprising an effective amount of valsartan prepared by wet granulation, exhibiting satisfactory disintegration properties and coated with one or more non-functional coating layers comprising film forming agents, adhesion promoting agents, coating agents, plasticizers, antitacking agents, coloring agents, opacifiers or mixtures thereof. US Patent Publication 20070166372 discusses a coprecipitate of amorphous valsartan with a pharmaceutically acceptable carrier, wherein the weight ratio of amorphous valsartan to the carrier ranges from 1:0.1 to 0.1:1. The tablet core comprising the coprecipitate is further film coated. The coated solid dosage forms of valsartan discussed are coated primarily with aqueous based film coating compositions, but however do not comprise more than even 10-20% by weight of hydrophilic swelling polymers in the tablet core.

Film coating is generally employed as a method of enhancing the product to positively impact patient preference, differentiating the product's visual appearance, as well as improving the ability to swallow. Aqueous film coating compositions are usually preferred for such coatings. However, depending on the excipients used and type of the dosage form, the aqueous film coating systems have been observed to have detrimental impact on the dosage form, the functions of the excipients used and the final desired performance of the formulation. Particularly, dosage forms of valsartan comprising not less than 25% by weight of core composition of hydrophilic swelling polymers have been observed to be affected by aqueous film coating compositions. The aqueous systems used may affect the properties of the polymers or excipients employed in the dosage forms and thereby such film coated dosage forms may have a rough and uneven surface appearance, reducing patient acceptability. The extended release formulations of valsartan of the gastroretentive type may also incorporate an effervescent couple comprising a gas generating agent and an acid source. Aqueous based film coating tends to impact the performance of such an effervescent couple as well. The impact of aqueous film coatings on the coated valsartan tablets discussed above may not be evident considering the type of those formulations and the type of excipients and amounts thereof they use. However, for systems of valsartan of the extended release type comprising high amounts of swelling polymers, aqueous based film coating systems can have detrimental impact on the desired function, appearance as well as release and gastroretentive profile of the dosage forms.

A need thus exists for development of coated extended release dosage forms of valsartan that have excellent physical appearance, increased patient acceptability and desired release and gastroretentive performance. The present inventors after in-depth research developed extended release coated formulations of valsartan comprising a core of valsartan and at least one swelling hydrophilic polymer and at least one coating layer over the core wherein the coating layer in contact with the core is applied using at least one organic solvent based coating composition.

The present inventors further also developed extended release coated formulations comprising a core of valsartan and a dual layer film coating system, that overcomes the problems associated with application of direct aqueous coating systems on extended release core tablets of valsartan, particularly core tablets comprising high amounts of swelling polymers. The present inventors have developed coated extended release formulations of valsartan comprising an extended release valsartan core and dual layer coating system comprising an inner organic seal coat layer in contact with the core and an outer aqueous film coating layer. Such dual coated extended release dosage forms of valsartan are aesthetic in appearance and have desired release and/or gastroretentive properties and excellent smooth surface, thereby enhancing patient acceptability and swallowability.

SUMMARY OF THE INVENTION

The present invention relates to coated extended release pharmaceutical formulations of valsartan. The invention further relates to extended release pharmaceutical formulations comprising a core comprising valsartan and at least one coating layer over the core. Particularly the present invention relates to extended release pharmaceutical formulations comprising (a) a core comprising valsartan and at least one swelling polymer and (b) at least one coating layer over the core wherein the coating layer in contact with the core is applied from an organic solvent based system. The present invention also relates to extended release pharmaceutical formulations comprising a core comprising valsartan and at least one swelling polymer and dual layer coating over the core.

DETAILED DESCRIPTION OF THE INVENTION

The present invention provides coated extended release dosage forms of valsartan that are aesthetically acceptable and easily swallowable.

The invention relates to extended release pharmaceutical formulations comprising a core comprising valsartan and at least one coating layer over the core. The present invention discloses extended release pharmaceutical formulations comprising (a) a core comprising valsartan, at least one hydrophilic swelling polymer, and at least one pharmaceutically acceptable excipient and (b) at least one coating layer. The present invention further relates to extended release pharmaceutical formulations comprising (a) a core comprising valsartan and at least one swelling polymer and (b) at least one coating layer over the core wherein the coating layer in contact with the core is applied from an organic solvent based system.

The term "biocompatible" as applied to swelling agents means agents that are useful in preparation of the said composition of this invention are polymers that are water soluble, nontoxic and swell in a dimensionally unrestricted manner upon imbibition of gastric fluid. The swelling agent used in the present invention includes one or more swellable biocompatible hydrophilic polymers. Preferably, the polymers are employed in the dry state or in a form that has substantial capacity for water uptake.

The term "composition" or "formulation" or "dosage form" has been employed interchangeably for the purpose of the present invention and means that it is a pharmaceutical formulation which is suitable for administration to a patient. For the purpose of the present invention, the terms "controlled release" or "sustained release" or "extended release" or "modified release" or "prolonged release" have been used interchangeably and mean broadly that the active agent is released at a predetermined rate that is different or slower than immediate release of the active agent.

Core:

The formulation of the present invention comprises a core comprising valsartan and at least one pharmaceutically acceptable excipient. In another embodiment, the formulation of the present invention comprises a core comprising valsartan, at least one hydrophilic swelling polymer and at least one pharmaceutically acceptable excipient.

The active ingredient for the purpose of this invention is valsartan. In a further embodiment, valsartan may be present in the formulations of the present invention in crystalline, substantially crystalline, amorphous, substantially amorphous, or dissolved form and the like or any combinations thereof. The crystalline form may have different polymorphs. All different polymorphs, solvates, hydrates, salts are within the purview of this invention. Also included within the scope of the present invention are the salts, esters, amides, prodrugs, active metabolites, analogs, and the like of valsartan. In one embodiment, valsartan is employed in the formulations of the present invention in an amount typically ranging from about 40 mg to about 640 mg. In a further embodiment, the amount of valsartan employed in the formulations of the present invention is from about 40 mg to about 320 mg. In another embodiment, the amount of valsartan employed in the formulations of the present invention is from about 80 mg to about 320 mg.

The valsartan may be present in an amount from about 1% to about 80% by weight of the composition. In one embodiment, the valsartan is present in an amount from about 2% to about 70% by weight of the composition. In another embodiment, the valsartan is present in an amount from about 5% to about 50% by weight of the composition.

The core comprising valsartan further comprises at least one hydrophilic swelling polymer and at least one pharmaceutically acceptable excipient.

In one embodiment, the hydrophilic swelling polymers that may be employed in the composition of the present invention, include but are not limited to, polyalkylene oxides, cellulosic polymers, acrylic acid polymers, maleic anhydride polymers; polymaleic acid, poly(acrylamides), poly(olefinic alcohol)s, poly(N-vinyl lactams), polyols, polyoxyethylated saccharides, polyoxazolines, polyvinylamines, polyvinyl alcohol, polyimines, polysaccharides, polyurethane hydrogels, zein, shellac-based polymers or derivatives or mixtures thereof. In a further embodiment, the hydrophilic polymers used as swelling agents in the compositions of the present invention are polymers that are nontoxic and swell in a dimensionally unrestricted manner upon imbibing gastric fluid. In one embodiment, the swelling agents are employed in the dry state or in a form that has substantial capacity for water uptake.

In an embodiment, useful hydrophilic polymers include, but are not limited to, polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch, polyvinyl alcohol, and mixtures thereof.

Cellulosic polymers and derivatives thereof employed in the composition of the present invention include, but are not limited to, methylcellulose, hydroxymethyl cellulose, hydroxypropylcellulose, hydroxyethylcellulose, hydroxypropylmethylcellulose, calcium carboxymethyl cellulose, sodium carboxymethylcellulose and the like or combinations thereof. In one embodiment, cellulosic polymers and derivatives thereof employed as hydrophilic swelling polymers in the dosage forms of the present invention include those with viscosity within the range of about 50 centipoise to about 2,00,000 centipoise for a 2% aqueous solution at 20° C. In another embodiment, cellulosic polymers and derivatives thereof employed as swelling agent in the dosage forms of the present invention include those with low viscosity within the range of about 50 centipoise to about 15,000 centipoise for a 2% aqueous solution at 20° C. In a further embodiment, the cellulosic polymers and derivatives thereof employed as swelling agent in the dosage forms of the present invention include those with high viscosity within the range of about 20,000 centipoise to about 2,00,000 centipoise for a 2% aqueous solution at 20° C.

Polyalkylene oxides and derivatives thereof employed in the compositions of the present invention include, but are not limited to, polyethylene oxide. In one embodiment, polyethylene oxide polymers employed in the compositions of the present invention have molecular weights of about 4,000,000 and higher. In another embodiment, polyethylene oxide polymers with molecular weights within the range of about 4,000,000 to about 10,000,000 are employed in the compositions of the present invention. In a further embodiment, polyethylene oxide polymers with molecular weights within the range of about 4,500,000 to about 9,000,000 are employed in the compositions of the present invention. In a further embodiment, polyethylene oxide polymers employed have viscosity in range of about 50 centipoise to about 2,000,000 centipoise, for a 2% aqueous solution at 20° C.

Polysaccharides and derivatives thereof employed in the compositions of the present invention include, but are not limited to, starch and starch-based polymers e.g. pre-gelatinized starch; chitosan; alginates; maltodextrin; polysaccharide gums such as, but not limited to, xanthan gum, guar gum, locust bean gum, fenugreek gum, galactomannans, gellan, konjac, guar gum, inulin, karaya gum; and the like or combinations thereof. In one embodiment the swelling agents employed in the compositions of the present invention include, but are not limited to, polyethylene oxide, hydroxypropyl cellulose, hydroxypropyl methyl cellulose, hydroxyethyl cellulose, sodium carboxymethyl cellulose, calcium carboxymethyl cellulose, methyl cellulose, polyacrylic acid, xanthan gum, polyvinyl alcohol or mixtures thereof. In one embodiment, the hydrophilic swelling polymer is present invention in not less than 15% by weight of the core. In a further embodiment, the hydrophilic swelling polymer is present in an amount of about 15% to about 95% by weight of the core. In a further embodiment, the amount of hydrophilic swelling polymer in the dosage form of the present invention is about 20% to about 90% by weight of the core. In one embodiment, the amount of hydrophilic swelling polymer in the dosage form of the present invention is about 25% to about 85% by weight of the core.

Pharmaceutically acceptable excipients that may further be employed in the compositions of the present invention include, but are not limited to, solubility enhancing agents, release retardants, swelling enhancers, acid source, gas generating agents, binders, lubricants, diluents, disintegrants, glidants, colorants, pH modifiers, pore-formers, and the like or mixtures thereof.

Suitable solubility enhancing agents that may be employed in the compositions of the present invention may be polymeric or non-polymeric in nature. Due to the low solubility of valsartan, the solubility enhancing agent is used to increase the solubility of valsartan. In a further embodiment, one or more solubility enhancing agents that may be employed include, but are not limited to, cationic, anionic, zwitterionic, nonionic, hydrophilic, hydrophobic or amphiphilic surfactants and the like or any combinations thereof. The ionic surfactants include, but are not limited to, alkylammonium salts; fusidic acid salts; fatty acid derivatives of amino acids, oligopeptides, or polypeptides; glyceride derivatives of amino acids; lecithins or hydrogenated lecithins; lysolecithins or hydrogenated lysolecithins; phospholipids or derivatives thereof; lysophospholipids or derivatives thereof; carnitine fatty acid ester salts; salts of alkylsulfates; fatty acid salts; sodium docusate; acyl lactylates; mono- or di-acetylated tartaric acid esters of mono- or di-glycerides; succinylated mono- or di-glycerides; citric acid esters of mono- or di-glycerides; or mixtures thereof. The amphiphilic surfactants include, but are not limited to, d-a-tocopheryl polyethylene glycol 1000 succinate and d-a-tocopherol acid salts such as succinate, acetate, etc. The non-ionic surfactants include, but are not limited to, fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols or sterol derivatives; polyethylene glycol alkyl ethers; sugar esters; sugar ethers; lactic acid derivatives of mono- or diglycerides; oil-soluble vitamins/vitamin derivatives; PEG fatty acid esters; polyglycerized fatty acid; polyoxyethylene-polyoxypropylene block copolymers; transesterification products of a polyol with at least one member of the group consisting of glycerides, vegetable oils, hydrogenated vegetable oils, fatty acids and sterols wherein the commonly used oils are castor oil or hydrogenated castor oil, or an edible vegetable oil such as corn oil, olive oil, peanut oil, palm kernel oil, almond oil and the commonly used polyols include glycerol, propylene glycol, ethylene glycol, polyethylene glycol, sorbitol and pentaerythritol; or mixtures thereof. In another embodiment of the present invention, the one or more solubilizers that may be employed include polyethylene-polyoxypropylene block copolymer (Lutrol® series BASF) and d-α-tocopheryl polyethylene glycol 1000 succinate (Vitamin E 25 TPGS® by Eastman) or combinations thereof. In one embodiment, valsartan in completely or partially solubilized form with one or more solubilizers is employed in the compositions of the present invention.

In an embodiment, the one or more solubilizers include, but are not limited to, PEG-20-glyceryl stearate, PEG-40 hydrogenated castor oil, PEG-6 corn oil, lauryl macrogol-32 glyceride, stearoyl macrogol glyceride, polyglyceryl-10 monodioleate, propylene glycol oleate, propylene glycol dioctanoate, propylene glycol caprylate/caprate, glyceryl monooleate, glycerol monolinoleate, glycerol monostearate, PEG-20 sorbitan monolaurate, PEG-4 lauryl ether, sucrose distearate, sucrose monopalmitate, polyoxyethylene-polyoxypropylene block copolymer, polyethylene glycol 660 hydroxystearate, sodium lauryl sulphate, sodium dodecyl sulphate, propylene glycol alginate, sodium taurocholate, sodium glycocholate, sodium deoxycholate, betains, polyethylene glycol, d-alpha-tocopheryl polyethylene glycol 1000 succinate, and mixtures thereof.

In one embodiment, in the compositions of the present invention valsartan and one or more solubilizers may be employed in different ratios. It is contemplated within the scope of the invention that the ratio of valsartan to solubilizers may range from about 50:1 to about 1:50. In one embodiment, the ratio of valsartan to solubilizers is from about 20:1 to about 1:20. In another embodiment, the ratio of valsartan to solubilizer is from about 10:1 to about 1:10. In a further embodiment, a combination of solubility enhancing agents may also be included where the total amount of solubility enhancing agent employed is maintained in the above-mentioned ratios.

It is contemplated within the scope of the invention that the processes employed for solubilization of valsartan may include but are not limited to melt granulation, solvent treatment, wet granulation, physical mixing or spray drying and the like or combinations thereof. In one embodiment valsartan may be completely or partially solubilized using the melt granulation method. The entire dose of the valsartan may be present in the solubilized form or alternatively part of the valsartan is present in solubilized form whereas the other part as non-solubilized form, the ratio of which can vary from 1:99 to 99:1.

Suitable release retardants that may be employed in the compositions of the present invention include, but are not limited to, polymeric release retardants, non-polymeric release retardants or any combinations thereof. Release retardants are excipients which by way of various mechanisms retard release of the active ingredient.

Polymeric release retardants that may be employed for the purpose of the present invention include, but are not limited to, cellulose derivatives; polyhydric alcohols; saccharides; gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. In one embodiment, the swelling polymers enlisted above may also function as release retardants. Non-polymeric release retardants employed for the purpose of the present invention include, but are not limited to, fats, oils, waxes, fatty acids, fatty acid esters, long chain monohydric alcohols and their esters or combinations thereof.

Cellulose derivatives include, but are not limited to, ethyl cellulose, methylcellulose, hydroxypropylmethylcellulose (HPMC), hydroxypropyl cellulose (HPC), hydroxyethyl cellulose, hydroxymethyl cellulose, hydroxypropyl ethylcellulose, carboxymethylethyl cellulose, carboxy-ethylcellulose, carboxymethyl hydroxyethylcellulose, hydroxyethylmethyl carboxymethyl cellulose, hydroxyethyl methyl cellulose, carboxymethyl cellulose (CMC), methylhydroxyethyl cellulose, methylhydroxypropyl cellulose, carboxymethyl sulfoethyl cellulose, sodium carboxymethyl cellulose, or combinations thereof. Suitable swelling enhancers that may be employed in the compositions of the present invention include, but are not limited to, low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch, sodium starch glycolate, sodium carboxymethyl starch and the like or combinations thereof. Swelling enhancers help the swelling agents to swell rapidly to a large extent resulting in an increase in the size of the tablet. The content of the swelling enhancer in the compositions of the present invention is about 5% to about 60% by weight of the dosage form. In one embodiment, the content of the swelling enhancer is about 10% to about 50% by weight of the dosage form.

In an embodiment, the one or swelling enhancers include, but are not limited to, low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, pregelatinised starch, sodium carboxymethyl starch, and mixtures thereof.

Suitable acidulants that may be employed include physiologically compatible water-soluble organic acids which decrease the pH of the dosage form microenvironment or alternatively of the gastrointestinal tract. In a further embodiment acidulants refer to aliphatic or aromatic, saturated or unsaturated, monobasic acid (monocarboxylic acid), dibasic acid (dicarboxylic acid) or tribasic acid (tricarboxylic acid), with preference given to a compound having 2-10, preferably 2-6 carbon atoms. Suitable examples of the monobasic acids include, but are not limited to, saturated aliphatic monocarboxylic acids such as, but not limited to, acetic acid, propionic acid, lactic acid and valeric acid, and monobasic amino acids such as glycine, alanine, valine, leucine and isoleucine. Suitable examples of the dibasic acid include, but are not limited to, saturated aliphatic dicarboxylic acids such as oxalic acid, malonic acid, succinic acid, glutaric acid and adipic acid, unsaturated aliphatic dicarboxylic acids such as, but not limited to, maleic acid and fumaric acid, aromatic dicarboxylic acids such as, but not limited to, phthalic acid, dibasic amino acids such as aspartic acid and glutamic acid, and hydroxy dibasic acids such as, but not limited to, malic acid and tartaric acid, Suitable examples of the tribasic acid include, but are not limited to, hydroxy tribasic acids such as, but not limited to, citric acid. Suitable organic acid may be included in the form of a salt. Suitable examples of the salt of the organic acid include, but are not limited to, alkali metal salts such as, but not limited to, sodium salt and potassium salt, alkaline earth metal salts such as, but not limited to, calcium salt, and organic salts such as, but not limited to, ammonium salt. In one embodiment, the amount of the acidulant in the dosage form of the present invention is about 0.5% to about 20% by weight of the dosage form.

According to the present invention, the core can further comprise at least one gas generating agent. The gas generating agents also referred to as effervescent agent aid in the formation of highly porous structure that may enhance the buoyancy of the formulation. The gas generating agent employed for the purpose of the present invention is selected from, but not limited to, alkali and alkaline-earth metal carbonates and bicarbonates such as, but not limited to, sodium bicarbonate, sodium glycine carbonate, potassium bicarbonate, ammonium bicarbonate, sodium bisulfite, sodium metabisulfite, sodium carbonate, potassium carbonate and the like or combinations thereof. In one embodiment, the gas generating agent is sodium bicarbonate. In one embodiment, in a dry granulation process, the gas generating agent may be incorporated into the active core by blending it into the expanding composition before or after first compaction. In a further embodiment, when a wet granulation process is employed, it may be provided as an extra-granular constituent after wet granulation.

The core of the present invention typically may also include other pharmaceutically acceptable excipients such as, but not limited to, binders, lubricants, diluents, disintegrants, glidants, colorants, pore-former and the like or combinations thereof. Examples of suitable binders that may be incorporated include, but are not limited to, starch, pregelatinized starch, polyvinyl prrolidone, copovidone, cellulose derivatives, such as hydroxypropylmethyl cellulose, hydroxypropyl cellulose and carboxymethyl cellulose and their salts and the like or combinations thereof. Examples of suitable diluents include, but are not limited to, starch, dicalcium phosphate, microcrystalline cellulose, lactose monohydrate, dextrate hydrated and the like or combinations thereof. Examples of suitable lubricants include, but are not limited to, magnesium stearate, calcium stearate, stearic acid, talc, and sodium stearyl fumarate and the like or combinations thereof. Compositions of the present invention may optionally also include a glidant such as, but not limited to, colloidal silica, silica gel, precipitated silica, and the like or combinations thereof. Suitable disintegrants employed in the compositions of the present invention include, but are not limited to, croscarmellose sodium, crospovidone, sodium starch glycolate, starch, and the like or combinations thereof. An exemplary pore forming agent includes non-GMO dextrates.

In one embodiment, the core of the extended release formulation of valsartan may be of, but not limited to, a conventional non-gastroretentive controlled release matrix type, or gastroretentive controlled release matrix type and the like. In a further embodiment the core comprising valsartan is in the form of a tablet.

In a further embodiment, the core of the present invention delivers valsartan in an extended release manner. In another embodiment the extended release formulation of the present invention is in the form of a gastroretentive core. For the purpose of the present invention the term "gastroretentive" or "gastric retention" or "gastroretention" or "retained in upper gastrointestinal tract" when used with respect to the dosage form or core of the present invention, means that the dosage form or the core or at least a portion thereof remains in the upper gastrointestinal tract including stomach, for about 30 minutes or more.

In a further embodiment, the core as per the present invention may be in the form of a monolithic system, an expanding monolithic, bilayered, multilayered or in-lay system for oral administration which is adapted to deliver the active agent in a modified manner over extended period and further coated with at least one coating layer.

Valsartan may be incorporated in monolithic matrix of extended release core. In one embodiment, the active core of the present invention is multi-layered. In another embodiment, the active core of the present invention is a bilayered system comprising an active layer and a gastroretentive layer. In a further embodiment, valsartan is incorporated in the active layer of a bilayered extended release gastroretentive core comprising a active layer and a gastroretentive expanding layer wherein the actives released in a sustained manner over a desired time period from the active layer. In another embodiment, the bilayered gastroretentive core comprises a) an active layer comprising valsartan, at least one solubility enhancer, at least one release retardant, at least one pharmaceutically acceptable excipient and optionally at least one swelling agent; and b) a gastroretentive layer comprising at least one hydrophilic swelling polymer, at least one swelling enhancer and at least one pharmaceutically acceptable excipient. In a further embodiment, the bilayered gastroretentive core comprises a) an active layer comprising valsartan, at least one solubility enhancer, at least one release retardant, at least one pharmaceutically acceptable excipient and optionally at least one swelling agent; and b) a gastroretentive layer comprising at least one hydrophilic swelling polymer, at least one swelling enhancer, at least one gas generating agent, at least one acidulant and at least one pharmaceutically acceptable excipient. In a further embodiment, the gastroretentive core is multilayered comprising at least one active layer and at least one gastroretentive layer. In a further embodiment the active core is in the form of an expanding bilayered system for oral administration to deliver valsartan or different anti-hypertensive active from a first layer immediately upon reaching the gastrointestinal tract, and to deliver valsartan from a second layer, in a sustained manner over a specific time period. The second layer is also adapted to provide expanding nature for the dosage system, thereby making the dosage system have greater retention in the upper gastrointestinal tract. In yet another embodiment, the extended release gastroretentive active core is in the form of a trilayered system consisting of a drug layer compressed between a first gastroretentive layer and a second gastroretentive layer wherein valsartan is released in a sustained manner from the drug layer. In a further embodiment, the extended release gastroretentive active core is in the form of a trilayered system consisting of an immediate release layer designed to deliver valsartan or different anti-hypertensive active immediately upon reaching the gastrointestinal tract, a sustained release layer adapted to deliver the valsartan in a sustained manner over a desired time period and a gastroretentive layer designed to cause retention of the dosage form in the upper gastrointestinal tract.

Tablets cores in accordance with the present invention may be manufactured using conventional techniques of common tableting methods known in the art such as direct compression, dry granulation, wet granulation, melt granulation/extrusion or combinations thereof.

Further, in one embodiment, the present invention provides a process of preparing an extended release core comprising: preparing solubilized valsartan by treatment with solubility enhancing agent; blending said solubilized valsartan with at least one release retardant, at least one hydrophilic swelling polymer, and at least one pharmaceutically acceptable excipient; lubricating the blend to form a lubricated blend; compressing the blend to form a monolithic solid dosage form. In another embodiment, the present invention provides a process of preparing an extended release gastroretentive core comprising: preparing solubilized valsartan by treatment with solubility enhancing agent; blending said solubilized valsartan with at least one release retardant, at least one hydrophilic swelling polymer and at least one pharmaceutically acceptable excipient; lubricating the blend to form a lubricated blend; compressing the blend to form a monolithic active core. Furthermore, the present invention also provides a process of preparing an extended release gastroretentive active core of valsartan comprising: preparing solubilized valsartan by treatment with solubility enhancing agent; blending said solubilized valsartan with at least one release retardant, at least one hydrophilic swelling polymer and at least one pharmaceutically acceptable excipient, lubricating the blend to form drug layer blend; blending at least one hydrophilic swelling polymert, at least one pharmaceutically acceptable excipient, lubricating the blend to form a gastroretentive layer blend; and compressing the drug layer and the gastroretentive layer blends to form a bilayer core. In one embodiment, not more than about 40% valsartan is released from the extended release formulations of the present invention in 1 hour and not less than 75% valsartan is released over 8 hours.

In a further embodiment, the core may deliver one or more additional anti-hypertensive agents in addition to valsartan, Suitable anti-hypertensive agents that may be employed include, but are not limited to, hydrochlorothiazide, calcium blockers, beta-blockers, ACE inhibitors, inotropic agents, hypolipidemic agents, and/or rennin inhibitors. The additional anti-hypertensive agent may be delivered in immediate or extended release manner.

Coatings:

The extended release pharmaceutical formulations of the present invention comprise a core of valsartan, which is further coated with at least one coating layer. In one embodiment, the coating layer in contact with the core is applied from an organic solvent based system.

In one embodiment, the one or more coating layers comprise at least one coating agent and at least one pharmaceutically acceptable coating excipient.

In another embodiment, coating agent employed in the coating layers of the present invention includes, but is not limited to, polymeric and/or non-polymeric coating agent. Such a polymeric coating agent includes, but is not limited to, hydroxypropyl methyl cellulose (HPMC), hydroxypropyl cellulose (HPC), hydroxyethyl cellulose, hydroxymethyl cellulose, hydroxypropyl ethylcellulose, ethyl cellulose, polyvinylacetate, copolymers of polyvinyl alcohol, polyvinylpyrrolidone, polyethylene glycol or combinations thereof. The non-polymeric coating agent includes, but is not limited to, fats, oils, waxes, fatty acids, fatty acid esters, long chain monohydric alcohols and their esters, phospholipids, terpenes or combinations thereof.

In another embodiment, at least one pharmaceutically acceptable coating excipient employed in the one or more coating layer/s of the present invention includes, but is not limited to, plasticizers, anti-tacking agents, opacifiers or colorants, and the like or combinations thereof. Suitable plasticizers that may be employed include, but are not limited to, polyethylene glycol, polyethylene glycol derivatives, triacetin, dibutyl sebacate, diethyl phthalate, propylene glycol, glycerin, liquid paraffin, triethyl citrate, and mixtures thereof. Anti-tacking agents that may be employed include, but are not limited to, talc, glyceryl monostearate, silicon dioxide and metallic stearates such as magnesium stearate, or the like. Opacifier(s)/colorant(s) that may be employed include, but are not limited to, titanium dioxide, dyes, natural colors, lake colors, oxide colours or combinations thereof. In one embodiment, pH modifiers may be employed in the systems used for coating in the present invention, such as but not limited to, bicarbonate, carbonate, phosphate, or hydroxide of sodium or potassium, magnesium carbonate, magnesium hydroxide, ammonium carbonate, ammonium bicarbonate, magnesium oxide, calcium hydroxide, or mixtures thereof.

In one embodiment, preformed coating systems such as, but not limited to, Opadry Clear 03K19229, Opadry 200 Blue 200F105000, Kollicoat® Protect, Kollicoat® Smartseal 30D, Aquarius® MG and the like or combinations thereof may be employed as coatings for the compositions of the present invention.

In a further embodiment, the one or more coating layers are applied on the core using at least one coating composition comprising the above mentioned at least one coating agent and at least one pharmaceutically acceptable excipient in solution or dispersion in at least one solvent. In another embodiment, solvents employed for the coating composition are aqueous, organic or any combinations thereof.

In one embodiment, organic solvents such as, but not limited to, methanol, isopropanol, ethanol, acetone, methylene chloride, ethyl acetate, and the like or combinations thereof may be employed. In a further embodiment, organic solvents may be employed for coating in combination with purified water. In another embodiment, water may be employed for coating.

In one embodiment, the coating layer in contact with the core is applied from an organic solvent based system. Without being bound to any theory, it is believed that the coating layer in contact with the core when applied using an aqueous coating composition results in tablets with a rough surface due to interaction of the high amounts of swelling hydrophilic polymers with water. An interaction of swelling hydrophilic polymers with the aqueous coating composition during the coating stage is also believed to reduce the ability of the hydrophilic swelling polymers to either control drug release or cause retention of the dosage form in the upper gastrointestinal tract or both. In addition it is believed that an effervescent couple comprising at least one gas generating agent and at least one acidulant which may be incorporated in the core is likely to lose its functionality upon exposure to aqueous coating composition, thereby affecting the performance of the dosage form. However, the coating layer in direct contact with the core when applied from an organic solvent based system does not impact the appearance and/or the performance of the extended release formulation of the present invention. In one embodiment, organic solvent based system comprises only organic solvent or mixture of organic solvents and water. In one embodiment, when a combination of organic solvents and water is used for the layer in contact with the core, their proportion with respect to each other is not less than 1:1. In a further embodiment, for the coating layer in direct contact with the core, the organic solvent and water are used during coating in a proportion of not less than 75% of the total solvent system being used for preparation of the coating.

In one embodiment, the coating layers not in direct contact with the core may be applied from an organic solvent based system or aqueous system. In a further embodiment, the aqueous based system that may be employed for coating comprises water or mixture of organic solvents and water in a proportion of not more than 1:1.

In a further embodiment of the present invention, the core of valsartan as discussed above is coated with a dual coating system. In one embodiment, the core comprising valsartan is coated with two coating layers. In another embodiment, the dual coating system comprises the inner organic seal coating layer and the outer aqueous film coating layer. In one embodiment, the core of valsartan is coated with an inner organic seal coating layer and an outer aqueous film coating layer.

In a further embodiment, the term "inner organic seal coat layer" used herein refers to coating layer applied using organic solvents or a combination of aqueous and organic solvents. In one embodiment, when a combination of aqueous and organic solvents is used, the organic solvent is present in a proportion of more than 75% of the solvent being used for preparation of the coating system. In another embodiment, the term "outer aqueous film coating layer" refers to the coating layer applied using aqueous systems. Without being bound to any theory it is believed that inner organic seal coating layer of the dual layer coating system forms a layer physically separating the polymers of core and the aqueous coating layer, thus minimizing the interaction of the aqueous outer coating system with the various polymers, present in the core, particularly reduces the interaction with hydrophilic swelling polymers employed in the core, thereby providing tablets with uniform surface appearance and desired release and retention properties.

In one embodiment, the inner organic seal coating layer comprises hydroxypropyl methyl cellulose. In a further embodiment, the outer coating layer comprises polyvinyl alcohol.

One or more coatings on the core may be done by any of the techniques known in the art such as, but not limited to, fluid bed coating, pan coating, spray drying and the like. In a further embodiment, the coatings may be applied to the core in any suitable equipment where coating can be achieved.

In one embodiment, core comprising valsartan is coated with one or more coating layers to a weight gain in the range from about 0.1% to about 10% by weight of the tablet core. In a further embodiment, core comprising valsartan is coated with one or more coating layers to a weight gain in the range from about 0.25% to about 7.5% by weight of the tablet core. In another embodiment, core comprising valsartan is coated with one or more coating layers to a weight gain in the range from about 0.5% to about 5% by weight of the tablet core.

In a further embodiment, one or more coating layers employed for coating the valsartan containing core are non-functional film coatings. In another embodiment, the one or more coating layers completely cover the tablet core comprising valsartan.

In a further embodiment is provided the use of coated extended release pharmaceutical composition of valsartan of the present invention for the manufacture of a medicament for treatment of hypertension and heart failure. In one embodiment, the present invention provides a method for treatment of hypertension and heart failure comprising administering to the subject in need thereof coated extended release pharmaceutical compositions of valsartan of the present invention. In another embodiment, the present invention provides a method for reducing the risk of fatal and nonfatal cardiovascular events; primarily strokes and myocardial infarctions, comprising administering to the subject in need thereof coated extended release pharmaceutical compositions of valsartan of the present invention.

While the present invention has been described in terms of its specific embodiments, certain modifications and equivalents will be apparent to those skilled in the art and are intended to be included within the scope of the present invention. The invention is further illustrated by the following examples, which are for illustrative purposes and should not be construed as limiting the scope of the invention in any way.

Examples

Example 1: Coated Extended Release Formulations of Valsartan

A) Preparation of Core Tablets of Valsartan

TABLE 1

Composition of valsartan core tablets

| Ingredients | mg/unit |
|---|---|
| Active layer | |
| Valsartan | 160 |
| Vitamin E polyethylene glycol succinate | 80 |
| Poloxamer | 80 |
| Microcrystalline Cellulose | 135 |
| Hydroxypropyl methylcellulose | 110 |
| Calcium Silicate | 120 |
| Crospovidone | 35 |
| Fumaric Acid | 78 |
| Dextrates | 60 |
| Colloidal Silicon Dioxide | 10 |
| Magnesium Stearate | 20 |
| Ferric Oxide | 2 |
| Gastroretentive layer | |
| Polyethylene Oxide | 119 |
| Hydroxypropyl methyl cellulose | 119 |
| Hydroxyethyl Cellulose | 59 |
| Crospovidone | 120 |
| Microcrystalline Cellulose | 29 |
| Polyvinylpyrrolidone | 33 |
| 1-vinyl-2-pyrrolidone and vinyl acetate copolymer | 13 |
| Sodium Bicarbonate | 33 |
| Anhydrous Citric Acid | 10 |
| Magnesium Stearate | 5 |
| Isopropyl Alcohol | q.s. |
| Purified Water[#] | q.s. |
| Total | 1430 |

Procedure:

Preparation of Active Layer:

Valsartan is added to molten poloxamer and vitamin E polyethylene glycol succinate in a low shear mixer and mixed well. A part of microcrystalline cellulose, calcium silicate, fumaric acid and crospovidone are added to above mass and mixed further to get a homogeneous blend. All other ingredients are added to above mass and granulated to obtain granules of valsartan. These granules were then blended with other excipients except lubricant. The granules were then lubricated using magnesium stearate and compressed to form active layer blend.

Preparation of Gastroretentive Layer:

Povidone was dissolved in IPA: water mixture with overhead stirring. A part of polyethylene oxide, a part of hydroxyl propyl methyl cellulose, hydroxyethyl cellulose, a part of crospovidone, microcrystalline cellulose were passed through the sieve and dry mixed in rapid mixer. The binder solution was added to the dry mix and the mass was granulated and subsequently dried in a fluidized bed dryer to get desired loss on drying. Sized dried granules were blended with all other excipients including lactose, microcrystalline cellulose, sodium bicarbonate and citric acid. The granules were then lubricated using magnesium stearate to form gastroretentive layer blend.

Preparation of Bilayer Tablet:

A bilayer gastroretentive tablet of valsartan was prepared by compressing the active layer and the gastroretentive layer.

B) Aqueous Based Coating of Core Tablets

TABLE 2

Composition of the coating system

| Ingredients | mg/unit |
|---|---|
| Core tablets | 1430 |
| Coating system | |
| Polyvinyl Alcohol-based Opadry 200 Blue 200F105000 | 45 |
| Purified water# | q.s. |
| Total | 1475 | expelled during manufacturing process, not part of the final product

Procedure: All the ingredients of coating solution were dispersed well in purified water and kept on stirring while coating the core tablets. Coating was done to achieve weight gain level of 4%. The coated tablets were observed for physical appearance.

Observation: The coated tablets prepared as per the above procedure using an aqueous based coating system lacked aesthetic appeal and showed a rough surface. This appears to be due to the interaction of hydrophilic swelling polymers or effervescent couple with water when the aqueous coating composition is directly applied on the valsartan core tablets. Direct aqueous based coating on valsartan extended release core tablets comprising not less than 20% by weight of hydrophilic swelling polymers needs to be avoided.

Example 2: Coated Extended Release Formulations of Valsartan

The valsartan core tablets with composition as depicted in table 1 were coated with a dual coating system having an inner organic seal coating and outer aqueous film coating layer and of composition as depicted in table 3.

Dual Coating of Valsartan Core Tablets

TABLE 3

Composition of the dual coating system

| Ingredients | mg/unit |
|---|---|
| Valsartan core tablets | 1430 |
| Inner organic seal coating | |
| Hydroxyl propyl methyl cellulose | 12.615 |
| Triacetin | 1.26 |
| Talc | 1.125 |
| Isopropyl alcohol# | q.s. |
| Purified water# | q.s. |

TABLE 3-continued

Composition of the dual coating system

| Ingredients | mg/unit |
|---|---|
| Outer aqueous film coating | |
| Polyvinyl Alcohol-based Opadry 200 Blue 200F105000 | 45.00 |
| Purified water# | q.s. |
| Excipients (imprinting material) | |
| Opacode Black S-1-17823 | 0.104 |
| Isopropyl alcohol# | q.s. |
| Total | 1490 | expelled during manufacturing process, not part of the final product

Procedure: Talc was dispersed well in a mixture of isopropyl alcohol and purified water with the help of homogenizer to which triacetin was added. Hydroxyl propyl methyl cellulose was added to this mixture and dissolved to get the coating system. Coating was done to the core tablets to achieve 1% weight gain. These seal coated tablets were further coated with aqueous film coating composition prepared as per the procedure shown in table 2 to achieve a weight gain of 3%. The dual coated tablets were imprinted using imprinting material.

Observation: Application of 1% seal coating was effective in concealing the tablet surface before application of aqueous based film coating composition. Such dual coated tablets obtained had smooth surface, good aesthetic appeal and desired patient compliance.

Example 3. Coated Extended Release Formulations of Valsartan (160 mg Dose and 320 mg Dose)

Two embodiments of coated extended release formulations of valsartan having 160 mg and 320 mg respectively are depicted in Tables 4 and Table 5. Table 4 describes compositions of valsartan core tables. One of the procedures suitable for preparing such core tablets has been presented in Example 1. Table 5 describes compositions of the dual coating system. One of the procedures suitable for preparing such coating system has been presented in Example 4. The amount of ingredients listed in the Tables 1-5 are for the purpose of demonstration and are not intended to limiting. The precise amount of each ingredient depicted in the Examples and Tables can be adjusted based on needs and requirements.

TABLE 4

Compositions of valsartan core tablets (160 mg and 320 mg valsartan)

| Ingredients | mg/unit | mg/unit |
|---|---|---|
| Active layer | | |
| Valsartan | 160 | 320 |
| Vitamin E polyethylene glycol succinate | 80 | 160 |
| Poloxamer | 80 | 160 |
| Microcrystalline Cellulose | 135 | 270 |
| Hydroxypropyl methylcellulose | 110 | 220 |
| Calcium Silicate | 120 | 240 |
| Crospovidone | 35 | 70 |
| Fumaric Acid | 78 | 156 |
| Dextrates | 60 | 120 |
| Colloidal Silicon Dioxide | 10 | 20 |
| Magnesium Stearate | 20 | 40 |
| Ferric Oxide | 2 | 4 |

TABLE 4-continued

Compositions of valsartan core tablets (160 mg and 320 mg valsartan)

| Ingredients | mg/unit | mg/unit |
|---|---|---|
| Gastroretentive layer | | |
| Polyethylene Oxide | 119 | 238 |
| Hydroxypropyl methyl cellulose | 119 | 238 |
| Hydroxyethyl Cellulose | 59 | 118 |
| Crospovidone | 120 | 240 |
| Microcrystalline Cellulose | 29 | 38 |
| Polyvinylpyrrolidone | 33 | 66 |
| 1-vinyl-2-pyrrolidone and vinyl acetate copolymer | 13 | 26 |
| Sodium Bicarbonate | 33 | 66 |
| Anhydrous Citric Acid | 10 | 20 |
| Magnesium Stearate | 5 | 10 |
| Isopropyl Alcohol | q.s. | q.s. |
| Purified Water# | q.s. | q.s. |
| Total | 1430 | 2860 |

TABLE 5

Compositions of the dual coating systems

| Ingredients | mg/unit | mg/unit |
|---|---|---|
| Valsartan core tablets | 1430 | 2860 |
| Seal coating | | |
| Opadry Clear 03K19229 | 15.00 | 30.00 |
| Isopropyl alcohol# | q.s. | q.s. |
| Purified water# | q.s. | q.s. |
| Film coating | | |
| Polyvinyl Alcohol-based Opadry 200 Blue 200F105000 | 45.00 | 90.00 |
| Purified water# | q.s. | q.s. |
| Excipients (imprinting material) | | |
| Opacode Black S-1-17823 | 0.104 | 0.208 |
| Isopropyl alcohol# | q.s. | q.s. |
| Total | 1490 | 2980 |

We claim:

1. A controlled release gastroretentive oral dosage form, comprising:
a core comprising
(a) a therapeutically effective amount of valsartan of about 160 mg;
(b1) alpha-tocopherol polyethylene glycol succinate in an amount of about 80 mg;
(b2) polyoxyethylene polyoxypropylene block copolymer in an amount of about 80 mg;
(c1) polyethylene oxide in an amount of about 120 mg;
(c2) hydroxypropyl methylcellulose in an amount of about 230 mg;
(c3) hydroxyethylcellulose in an amount of about 60 mg;
(d) cross-linked polyvinyl pyrrolidone in an amount of about 150 mg;
(e) dextrates in an amount of about 60 mg; and
(f) a pharmaceutically acceptable carrier; and
a dual coating system surrounding the core;
wherein the dual coating system comprises a seal coating layer contacting the core and a film coating layer contacting the seal coating layer; wherein the core is a bilayered gastroretentive core comprising an active layer containing valsartan, and a gastroretentive layer; wherein no more than 40% valsartan is released from the oral dosage from in 1 hour and not less than 75% valsartan is released over 8 hours.

2. The oral dosage form of claim 1, further comprising:
(g) microcrystalline cellulose in an amount of about 160 mg.

3. A controlled release gastroretentive oral dosage form, comprising a core comprising:
(a) a therapeutically effective amount of valsartan from about 160 mg to about 320 mg;
(b) one or more solubilizers in a total amount of the one or more solubilizers from about 160 mg to about 320 mg;
(c) one or more biocompatible swelling agents in a total amount of the one or more swelling agents from about 300 mg to about 600 mg; and
(d) one or more swelling enhancers in a total amount of the swelling agents from about 150 mg to about 300 mg; and
a dual coating system surrounding the core;
wherein the dual coating system comprises a seal coating layer contacting the core and a film coating layer contacting the seal coating layer; wherein the core is a bilayered gastroretentive core comprising an active layer containing valsartan, and a gastroretentive layer; wherein no more than 40% valsartan is released from the oral dosage from in 1 hour and not less than 75% valsartan is released over 8 hours.

4. The oral dosage form of claim 3, further comprising (e) a pore forming agent in an amount from about 60 mg to about 120 mg.

5. The oral dosage form of claim 3, wherein said one or more solubilizers (b) is selected from the group consisting of hydrophilic surfactants, lipophilic surfactants, and mixtures thereof.

6. The oral dosage form of claim 3, wherein said one or more solubilizers (b) is selected from the group consisting of PEG-20-glyceryl stearate, PEG-40 hydrogenated castor oil, PEG-6 corn oil, lauryl macrogol-32 glyceride, stearoyl macrogol glyceride, polyglyceryl-10 monodioleate, propylene glycol oleate, propylene glycol dioctanoate, propylene glycol caprylate/caprate, glyceryl monooleate, glycerol monolinoleate, glycerol monostearate, PEG-20 sorbitan monolaurate, PEG-4 lauryl ether, sucrose distearate, sucrose monopalmitate, polyoxyethylene-polyoxypropylene block copolymer, polyethylene glycol 660 hydroxystearate, sodium lauryl sulphate, sodium dodecyl sulphate, propylene glycol alginate, sodium taurocholate, sodium glycocholate, sodium deoxycholate, betains, polyethylene glycol, d-alpha-tocopheryl polyethylene glycol 1000 succinate, and mixtures thereof.

7. The oral dosage form of claim 3, wherein said one or more biocompatible swelling agents (c) is a hydrophilic polymer.

8. The oral dosage form of claim 7, wherein said hydrophilic polymer is selected from the group consisting of polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch, polyvinyl alcohol, and mixtures thereof.

9. The oral dosage form of claim 3, wherein said one or more swelling agent is polyethylene oxide.

10. The oral dosage form of claim 3, wherein said one or more swelling enhancers (d) is selected from the group consisting of low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, pregelatinised starch, sodium carboxymethyl starch, and mixtures thereof.

11. The oral dosage form of claim 3, wherein said one or more swelling enhancers is cross-linked polyvinyl pyrrolidone.

12. The oral dosage form of claim 3, wherein said dosage form is retained in the upper gastrointestinal tract of a patient for a time period of about 1 hour to about 12 hours.

13. The oral dosage form of claim 3, further comprising one or more gas-generating agents.

14. The oral dosage form of claim 13, wherein said one or more gas-generating agents is sodium bicarbonate.

15. The oral dosage form of claim 3, further comprising a pharmaceutically acceptable carrier.

16. The oral dosage form of claim 3, wherein the coating layers comprise at least one coating agent and at least one pharmaceutically acceptable coating excipient.

17. The oral dosage form of claim 16, wherein the coating agent is a polymeric or non-polymeric coating agent or a combination thereof.

18. The oral dosage form of claim 17, wherein the polyermic coating agent is hydroxypropyl methyl cellulose, hydroxypropyl cellulose, hydroxyethyl cellulose, hydroxymethyl cellulose, hydroxypropyl ethylcellulose, ethyl cellulose, polyvinylacetate, copolymers of polyvinyl alcohol, polyvinylpyrrolidone, polyethylene glycol, or any combinations thereof.

19. The oral dosage form of claim 16, wherein the pharmaceutically acceptable coating excipient is a plasticizer, an anti-tacking agent, an opacifier, or a colorant; or any combinations thereof.

20. The oral dosage form of claim 3, wherein the inner and outer coating layers each comprise at least one coating agent and at least one pharmaceutically acceptable coating excipient.

21. The oral dosage form of claim 20, wherein the coating agent is hydroxypropyl methyl cellulose, hydroxypropyl cellulose, hydroxyethyl cellulose, hydroxymethyl cellulose, hydroxypropyl ethyl cellulose, ethyl cellulose, polyvinylacetate, copolymers of polyvinyl alcohol, polyvinylpyrrolidone, polyethylene glycol, or any combinations thereof.

22. The oral dosage form of claim 20, wherein the pharmaceutically acceptable coating excipient is a plasticizer, an anti-tacking agent, an opacifier, or a colorant; or any combinations thereof.

23. The oral dosage form of claim 3, wherein the inner organic seal coating layer comprises hydroxypropylmethyl cellulose.

24. The oral dosage form of claim 3, wherein the outer aqueous based film coating layer comprises polyvinyl alcohol.

25. The oral dosage form of claim 1, wherein the coating layers comprise at least one coating agent and at least one pharmaceutically acceptable coating excipient.

* * * * *

UNITED STATES PATENT AND TRADEMARK OFFICE
CERTIFICATE OF CORRECTION

| | | |
|---|---|---|
| PATENT NO. | : 9,675,585 B1 | Page 1 of 1 |
| APPLICATION NO. | : 15/080158 | |
| DATED | : June 13, 2017 | |
| INVENTOR(S) | : Joseph A. Fix et al. | |

It is certified that error appears in the above-identified patent and that said Letters Patent is hereby corrected as shown below:

In the Claims

In Claim 1, Column 18, Line 2, change "from" to --form--.

In Claim 3, Column 18, Line 27, change "from" to --form--.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*